US 6,207,853 B1

(12) United States Patent
Burk et al.

(10) Patent No.: US 6,207,853 B1
(45) Date of Patent: Mar. 27, 2001

(54) HOMOGENEOUS ASYMMETRIC HYDROGENATION USING PHOSPHINE LIGANDS OF TRANSITION METALS

(75) Inventors: Mark Joseph Burk, Cambridge (GB); Frank Bienewald, Versailles (FR); Martin Edward Fox; Antonio Zanotti-Gerosa, both of Cambridge (GB)

(73) Assignee: Chirotech Technology, Inc. (GB)

( * ) Notice: Subject to any disclaimer, the term of this patent is extended or adjusted under 35 U.S.C. 154(b) by 0 days.

(21) Appl. No.: 09/213,745

(22) Filed: Dec. 17, 1998

Related U.S. Application Data

(60) Provisional application No. 60/075,474, filed on Feb. 20, 1998, and provisional application No. 60/087,451, filed on Jun. 1, 1998.

(51) Int. Cl.[7] .................................................. C07C 69/76

(52) U.S. Cl. .............................. 560/61; 560/81; 560/85; 560/87; 560/115; 560/127; 560/193; 562/205; 562/401

(58) Field of Search ................... 560/61, 81, 87, 560/115, 127, 190, 193, 85; 502/155, 213; 562/401, 205, 410; 536/18

(56) References Cited

U.S. PATENT DOCUMENTS

| 4,939,288 | 7/1990 | Talley. |
|---|---|---|
| 5,008,457 | 4/1991 | Burk. |
| 5,171,892 | 12/1992 | Burk. |
| 5,936,109 | * 8/1999 | Berens. |

OTHER PUBLICATIONS

Burk, M.J., John E. Feaster, William A. Nugent, Richard L. Harlow (1993) "Preparation and Use of C$_2$–Symmetric Bis(phospholanes): Production of α–Amino Acid Derivatives via Highly Enantioselective Hydrogenation Reactions" Journal of the American Chemical Society, 115(22):10125–10138.

Burk, M.J., Michael F. Gross, Jose P. Martinez (1995) "Asymmetric Catalytic Synthesis of β–Branched Amino Acids via Highly Enantioselective Hydrogenation Reactions" Journal of the American Chemical Society 117(36):9375–9376.

Burk, M.J., Yan Ming Wang, Jeffrey R. Lee (1996) "A Convenient Asymmetric Synthesis of α–1–Arylalkylamines through the Enantioselective Hydrogenation of Enamides" Journal of the American Chemical Society 118(21):5142–5143.

Morimoto, Toshiaki, Mitsuo Chiba, Kazuo Achiwa (1989) "Highly Efficient Asymmetric Hydrogenation of Itaconic Acid Derivatives Catalyzed by a Modified Diop–Rhodium Complex" Tetrahedron Letters 30(6):735–738.

Kuwano, Ryoichi, Masaya Sawamura, Yoshihiko Ito (1995) "Catalytic Asymmetric Hydrogenation of Dimethyl Itaconate with Trans–Chelating Chiral Diphosphine Ligands TRAP–Rhodium Complexes" Tetrahedron: Asymmetry 6(10):2521–2526.

Organic Reactions: The Stobbe Condensation pp. 2–11.

Christopfel, W.C., B.D. Vineyard (1979) "Catalytic Asymmetric Hydrogenation with a Rhodium(I) Chiral Bisphosphine System. A Study of Itaconic Acid and Some of Its Derivatives and Homologues" Journal of the American Chemical Society 101(15):4406–4408.

Chiba, Takeshi, Akira Miyashita, Hiroyuki Nohira (1991) "Synthesis of Chiral Rh–Bichep Complexes, Highly Effcient Catalysts for Asymmetric Hydrogenations" Tetrahedron Letters 32(36):4745–4748.

(List continued on next page.)

Primary Examiner—James O. Wilson
Assistant Examiner—Robert W. Deemie
(74) Attorney, Agent, or Firm—Saliwanchik, Lloyd & Saliwanchik

(57) ABSTRACT

A process for the preparation of an enantiomerically enriched 2-substituted succinic acid derivative of formula 2, which comprises asymmetric hydrogenation of the dehydro precursor of formula 7 or 8, or a mixture thereof

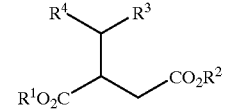

2

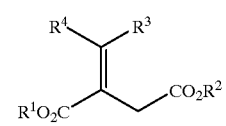

7

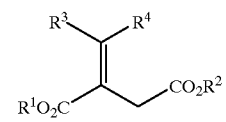

8 wherein $R^1$ and $R^2$ are independently H, a salt-forming cation, or an organic group of up to 30 C atoms, and $R^3$ and $R^4$ are independently H or an organic group of up to 30 C atoms, provided that $R^3$ and $R^4$ are not both H, in the presence of a transition metal complex of a chiral phosphine ligand having the partial formula 10

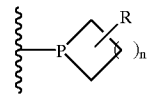

10 wherein n is 0 to 6 and R represents at least one non-hydrogen organic group of up to 30 C atoms.

48 Claims, No Drawings

OTHER PUBLICATIONS

Kawano, Hiroyuki, Youichi Ishii, Takao Ikariya, Masahiko Saburi, Sadao Yoshikawa, Yasuzo Uchida, Hidenori Kumobayashi (1987) "Ruthenium (II)–Binap Complex Catalyzed Asymmetric Hydrogenation of Unsaturated Dicarboxylic Acids" Tetrahedron Letters 28(17):1905–1908.

Ojima, Iwao, Testsuo Kogure (1978) "Effective Asymmetric Hydrogenation of Itaconic Acid Catalyzed by Neutral and Cationic Rhodium(I) Complexes with Chiral Pyrrolidino-diphosphine Ligand" Chemistry Letters, pp. 567–568.

Ojima, Iwao, Tetsuo Kogure (1978) "$^{31}$P NMR Studies on the Mechanism of Asymmetric Hydrogenation Catalyzed by Rhodium(I) Complexes with Chiral Pyrrolidinodiphosphine Ligand" Chemistry Letters, pp. 1145–1148.

Achiwa, Kazuo (1978) "Highly Enantioselective Catalytic Asymmetric Hydrogenation of Itaconic Acid [1)]" Tetrahedron Letters 17:1475–1476.

Shao, Liming, Shiro Miyata, Hitoshi Muramatsu, Hiroyuki Kawano, Youichi Ishii, Masahiko Saburi, Yasuzo Uchida (1990) "Asymmetric Synthesis of (R)–and (S)–4–(Substituted Benzyl)dihydrofuran–2(3H)–ones: An Application of the Ruthenium–binap † Complex–catalysed Asymmetric Hydrogenation of Alkylidenesuccinic Acids" Chem. Soc. Perkin Trans. 1, pp. 1441–1445.

Talley, John J., Cathleen E. Hanau, Gary A. DeCrescenzo, Michelle A. Schmidt "Application of Asymmetric Catalysis to the Synthesis of Peptide Mimics" in *Catalysis of Organic Reactions*, John R. Kosak and Thomas A. Johnson (eds.) (201 1994) pp. 81–90.

Jendralla, Heiner (1993) "Asymmetric Hydrogenation of 2–Benzylidenesuccinic Acid 4–[(4–BOC–amino)–1–piperidide] Monoamide: Key Step in a Process for Large Scale Preparation of a Renin Inhibitor" Papers, pp. 494–498.

\* cited by examiner

HOMOGENEOUS ASYMMETRIC HYDROGENATION USING PHOSPHINE LIGANDS OF TRANSITION METALS

CROSS-REFERENCE TO A RELATED APPLICATION

This application claims priority from provisional applications U.S. Ser. No. 60/075,474, filed Feb. 20, 1998 and U.S. Ser. No. 60/087,451, filed Jun. 1, 1998.

FIELD OF THE INVENTION

This invention relates to processes suitable for the large scale preparation of enantiomerically enriched 2-substituted succinic acid derivatives. In particular, it relates to asymmetric hydrogenation of isomeric mixtures of (E)- and (Z)-itaconate derivatives, as well as β,β-disubstituted itaconate derivatives, using a transition metal catalyst complex.

BACKGROUND OF THE INVENTION

Enantiomerically enriched 2-substituted succinic acids (see formulae 2a and 2b, below) have recently attracted interest as useful chiral building blocks and peptidomimetics in the design of pharmaceuticals, flavours and fragrances, and agrochemicals with improved properties. For example, the utility of 2-substituted succinic acid derivatives has been amply demonstrated through the synthesis of a range of new potent orally bioavailable drugs [J. J. Talley et al., in *Catalysis of Organic Reactions*, J. R. Kosak, T. A. Johnson (eds.), Marcel Dekker, Inc. (1994) Chapter 6; and H. Jendralla, *Synthesis* (1994) 494].

Chiral succinates can be prepared simply (e.g., via Stobbe condensation) from unsubstituted succinic esters and aldehydes or ketones, followed by asynmmetric hydrogenation of the intermediate β-substituted itaconate derivatives. The latter reaction may be represented as

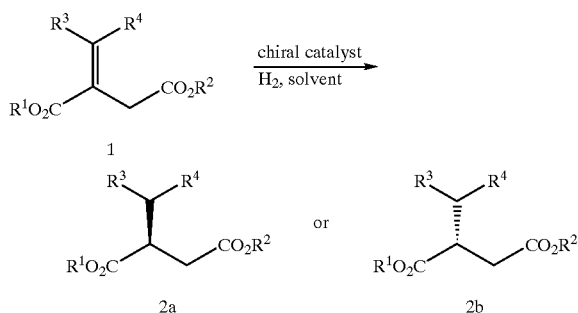

The unsubstituted parent substrate, itaconic acid (1, $R^1=R^2=R^3=R^4=H$), or its sodium salt, can be enantioselectively hydrogenated to 2-methylsuccinic acid with rhodium catalysts bearing the chiral ligand N-acyl-3,3'-bis(diphenylphosphino)pyrrolidine (BPPM) in up to 92% enantiomeric excess (ee) [I. Ojima et al., *Chem. Lett.*, 1978, 567; I. Ojima et al., *Chem. Lett.*, 1978, 1145; K. Achiwa, *Tetrahedron Lett.*, 1978, 1475]. A rhodium catalyst bearing the chiral diphosphine DIP AMP affords 2-methylsuccinate in up to 88% ee [W. C. Christofel, B. D. Vineyard, *J. Am. Chem. Soc.* 1979, 101, 4406; and U.S. Pat. No. 4,939,288]. Similar results have been obtained with a ruthenium catalyst containing the chiral diphosphine ligand BINAP [H. Kawano et al., *Tetrahedron Lett.*, 1987, 28, 1905]. Rhodium catalysts bearing modified DIOP ligands provide 2-methylsuccinic acid derivatives with variable enantioselectivities, between 7 and 91% ee. In these latter reactions, the ee value is very dependant on the rhodium catalyst precursor and whether the free acid or the ester is used [T. Morimoto et al., *Tetrahedron Lett.*, 1989, 30, 735]. Better results have been reported with a neutral rhodium catalyst of the chiral diphosphine 2,2'-bis(dicyclohexylphosphino)-6,6'-dimethyl-1,1'-biphenyl (BICHEP), whereby dimethylitaconate was hydrogenated in 99% ee [T. Chiba et al., *Tetrahedron Lett.*, 1991, 32, 4745].

In contrast to the success achieved with unsubstituted itaconate derivatives, asymmetric hydrogenation of β-substituted itaconic acid derivatives of general structure 3 and 4 ($R^3 \neq H$) has been more challenging; relatively few reports of high enantioselectivity (over 90% ee) have appeared. The curtailed effectiveness of known asymmetric catalysts for the hydrogenation of β-substituted itaconic acids derivatives 3 and/or 4 is particularly apparent when $R^3$ is an alkyl group, in which case no enantioselectivities above 90% ee have been reported.

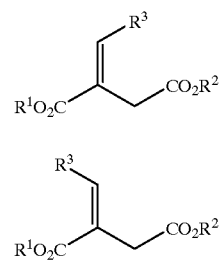

It should be noted that enantiomerically pure compounds are required for many applications in, for example, the pharmaceutical industry. Consequently, providing enantiomeric purity is the ultimate objective of an asymmetric process, and achieving high enantioselectivity in a transformation of the type described herein is crucial from a process standpoint. 90% ee is often selected as a lower acceptable limit, because compounds often may be purified to enantiomeric purity through recrystallisation when the initial value is above 90% ee. Enantiomeric excesses lower than 90% ee become increasingly more difficult to purify.

A major complication encountered with β-substituted itaconic acid derivatives is that they frequently are synthesised as a mixture of E and Z geometric isomers, i.e. formulae 3 and 4 respectively. This presents serious difficulties in subsequent hydrogenation reactions, since the different geometric isomers typically are reduced with vastly different rates and enantioselectivities. Accordingly, it has been necessary to separate the E- and Z-isomers (3 and 4) prior to the hydrogenation reaction. From a process standpoint, this is a wasteful, time-consuming, and yield-limiting feature.

Several reports have disclosed the ability to hydrogenate pure β-substituted (E)-itaconate derivatives (3). Even when the substrates are E-pure, however, high enantioselectivities have been limited to hydrogenation of β-arylitaconate derivatives (3, $R^3$=aromatic ring such as phenyl or naphthyl). Isomerically pure (E)-β-phenylitaconate derivatives have been hydrogenated with a DIPAMP-Rh catalyst in up to 97% ee [U.S. Pat. No. 4,939,288]. The same substrates were hydrogenated with a Ru-BINAP catalyst in up to 90% ee [H. Kawano et al., *Tetrahedron Lett.*, 1987, 28, 1905]. A rhodium complex bearing a modified DIOP ligand allowed hydrogenation of several (E)-β-arylitaconate derivatives with enantioselectivities up to 96% ee [T. Morimoto et al., *Tetrahedron Lett*, 1989, 30, 735].

Despite these impressive results, relatively poor enantioselectivities have been reported in the hydrogenation of (E)-pure β-alkylitaconate derivatives (3, $R^3$=alkyl). The DIPAMP-Rh catalyst noted above provided 2-isobutylsuccinate in only 76% ee through hydrogenation of (E)-substrate 3 ($R^3$=CH(CH$_3$)$_2$) [U.S. Pat. No. 4,939,288]. Importantly, it is indicated that the (Z)-isomer of this substrate (i.e., 4, $R^3$=CH(CH$_3$)$_2$) is not a suitable substrate for this reaction and must be separated from (E)-substrate prior to hydrogenation. The low enantioselectivity achieved with this particular substrate using known catalysts is regrettable since the product succinate 2 ($R^3$=CH(CH$_3$)$_2$) serves as a critical component of numerous new drug candidates.

Itaconate derivatives that possess two substituents in the β-position (β,β-disubstituted itaconates of formula 1 where $R^3,R^4 \neq H$) have thus far proven impossible to hydrogenate with high enantioselectivities and high rates. The only reported example of this type revealed that dimethyl β,β-dimethylitaconate may be hydrogenated with a Rh-TRAP catalyst system with the highest enantioselectivities being 78% ee [R. Kuwano et al., *Tetrahedron: Asymmetry*, 1995, 6, 2521].

SUMMARY OF THE INVENTION

One aspect of the present invention is based on the discovery that a broad variety of different itaconate derivatives can be readily hydrogenated using certain chiral mono and diphosphine-transitional metal catalysts, to afford highly enantiomerically enriched 2-substituted succinates. Another aspect of the present invention lies in the realisation that, when $R^3$ and/or $R^4$ has an α-H atom, an isomerised product is formed; this undesired product can be removed, once its presence is appreciated.

A further aspect of the present invention is based on the discovery that an efficient and high yielding preparation of an enantiomerically enriched 2-substituted succinic acid derivative (2), by asymmetric hydrogenation is the presence of a transition metal complex of a chiral phosphine, is facilitated by use of particular salt forms of the hydrogenation substrate.

Important characteristics of the present invention include: (i) the ability to hydrogenate β-alkyl-substituted itaconate derivatives with very high enantioselectivities, (ii) the ability to hydrogenate an isomeric mixture of (E)- and (Z)-itaconate derivatives with very high enantioselectivities, (iii) the ability to hydrogenate β,β-disubstituted itaconate derivatives with high enantioselectivities, (iv) the ability to hydrogenate specifically itaconate substrates in the presence of an isomerised (deconjugated) analogue of the substrate formed during substrate synthesis, (v) a convenient procedure for separation of the succinate products and remaining isomerised substrate leading to facile purification of the products, and (vi) an efficacious overall process encompassing the above features for the synthesis of enantiomerically pure 2-substituted succinate derivatives. Either enantiomer of the 2-substituted succinate derivative may be obtained by the method described herein.

In addition, for certain hydrogenation substrates, use of salt forms can have a number of advantages. Firstly, formation and isolation of a salt form may provide a convenient means of effecting substrate purification prior to hydrogenation, should this be required. Secondly, at a given molar ratio of substrate to catalyst (S/C ratio) and reaction time, a higher substrate conversion and/or higher enantioselectivity can be achieved. Thirdly, high reaction rates allow reactions to be performed at low temperatures, e.g. 0° C., whereby higher product enantiopurity is observed.

DESCRIPTION OF THE INVENTION

Both β-substituted and β,β-disubstituted itaconate derivatives may be prepared most readily by Stobbe condensation between dialkyl succinates 5 and aldehydes (6, $R^3$=H) or ketones (6, $R^3,R^4 \neq H$) in the presence of a base. A review article describing the Stobbe condensation may be found in *Org. React.*, 1951, 6, 1–73. In general, the Stobbe condensation leads to a mixture of E and Z isomeric itaconate derivatives 7 and 8, especially in the case where $R^3$ and/or $R^4$ are alkyl groups.

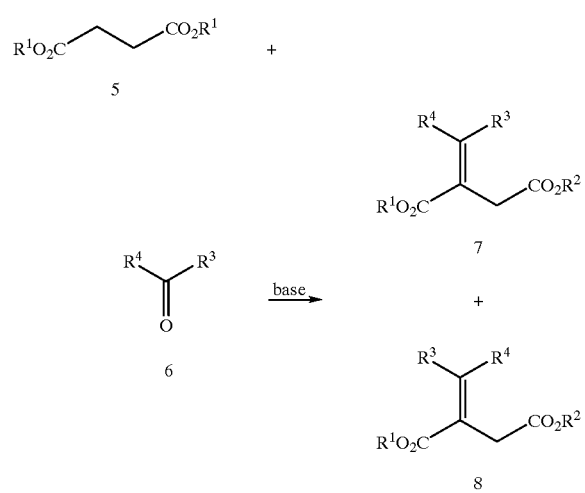

Typically, in products of the Stobbe condensation, $R^1$ is an esterifying group and $R^2$ is H. Such compounds are preferred starting materials for use in this invention.

Moreover, if $R^3$ or $R^4$ in aldehyde or ketone 6 contains a C—H group adjacent to the carbonyl (C=O) function, e.g. if $R^4$ is CHR$^5$R$^6$ where $R^5$ and $R^6$ are each H or any other group consistent with the definition of $R^4$, then a significant amount of isomerised (deconjugated) compound 9 may also be formed. In some cases, e.g. depending on the catalyst, this can be the major product of the Stobbe condensation reaction. The presence of isomerised compound 9 in the mixture is potentially detrimental, since any hydrogenation of this material will afford racemic succinate product.

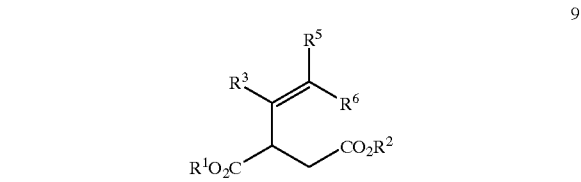

In accordance with the present invention, a mixture of Stobbe products composed of E and Z isomers 7 and 8, along with regioisomeric deconjugated compound 9, may be employed without any special purification in the hydrogenation reaction in which only the itaconate substrates 7 and 8 are reduced to desired succinate product (2a or 2b) with very high enantioselectivity. This stands in contrast to all previous processes in which only purified (E)-itaconate substrates could be employed in the hydrogenation procedure.

As a further aspect of the present invention, it has been discovered that a Stobbe product mixture of a β,β-disubstituted itaconate derivative (e.g., 7, $R^3,R^4 \neq H$) and regioisomer 9, can be treated such that only the itaconate derivative is hydrogenated to the desired succinate product (2a or 2b), with high enantioselectivity. No other catalyst system previously has been shown to allow asymmetric hydrogenation of β,β-disubstituted itaconate derivatives with high enantioselectivity.

Suitable substrates for the hydrogenation process outlined above are of the general structure 7 or 8, or a mixture thereof, wherein $R^1$, $R^2$, $R^3$ and $R^4$ can be independently H or an organic group of up to 30 C atoms, or $R^1$ and $R^2$ are a carbon, or $R^3$ and $R^4$ are joined to form a ring, provided that at least one of $R^3$ and $R^4$ is not H. In one embodiment, the invention provides an improved procedure in the case where one of $R^3$ and $R^4$ is H; typically, the other is $C_{1-20}$ alkyl or aralkyl. The fact that β,β-disubstituted itaconates can be effectively hydrogenated in this process means also that $R^3$ and $R^4$ may each be an organic group of up to 30 C atoms, e.g. $C_{1-20}$ alkyl or aralkyl, and preferably the same, or may be linked to form a ring, e.g. a saturated carbocyclic ring. $R^1$ is preferably $C_{1-10}$ alkyl or aralkyl, and $R^2$ is preferably H (or a cation).

If a salt of the precursor is used, it may be a salt form of either itaconate derivative which may be either β-substituted or β,β-disubstituted. In this case, $R^2$ may represent a metal, e.g. alkali metal, or other cation. Typically, this is formed in situ, by introducing a strong base such as a metal alkoxide, e.g. NaOMe. This may be used in a sub-stoichiometric amount, e.g. a catalytic quantity.

Alternatively, the salt may be formed with, for example, a counterion $YH^+$ such as that derived from an amine Y or a phosphine Y. Primary $C_{1-10}$ alkylamines and cycloalkylamines are preferred, in particular, tert-butylamine. Tertiary amines such as triethylamine may also be used.

Especially when an amine or phosphine salt is used, it is usually isolated prior to use in the process, but alternatively may be generated in situ. Isolation of the precursor salt can be advantageous as a means of effecting substrate purification, usually by crystallisation, e.g. to remove any regioisomeric contaminants. However, this step is not always necessary, especially when the Stobbe condensation is carried out under carefully controlled conditions where regioisomeric contaminants are not formed, e.g. at a temperature of around 5° C. rather than at normal room temperature.

Temperature effects may also be noted in the process of the present invention, with a lowering of reaction temperature resulting in improved enantioselectivities for certain substrates, e.g. when $R^3/R^4$ is a cyclic group, or if the precursor is an amine or phosphine salt. Especially in such cases, the reaction temperature may be less than 10° C., and is preferably −25 to +5° C.

Catalysts that are suitable for the novel asymmetric hydrogenation process comprise a transition metal complexed to an appropriate chiral phosphine ligand. Preferably, the ligand is a monophosphine or diphosphine ligand which may be used in either enantiomeric form. The preferred transitional metal is rhodium; others that may be used include ruthenium and iridium.

Preferred phosphines are those incorporating an appropriately substituted phosphorus heterocycle of general structure 10, where n is zero or an integer 1 to 6, and where the carbocyclic framework of 10 is substituted with one or more R substituents such that the structure 10 is a chiral entity, and where the R substituent is an organic group of up to 20 C atoms, typically a $C_{1-10}$ linear or branched hydrocarbon substituent, but which also may contain heteroatoms. In the case where more than one R substituent is present in the structure 10, these R substituents may be the same or different, and may be joined to form ring systems fused with the parent carbocyclic framework illustrated for 10. Monophosphines containing the phosphorus heterocyclic unit 10 take the general structure 11, where R' is an organic group of up to 20 C atoms. Alternatively, two phosphorus heterocycles of structure 10 may be tethered with a linking unit to form a diphosphine of general structure 12, where the linking unit is an organic group of up to 30 C atoms, linear, branched or cyclic, hydrocarbon or heteroatomic in nature.

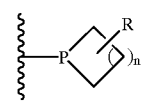

10

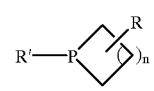

11

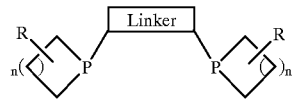

12

Examples of these ligands encompass 2,4-disubstituted phosphetanes 13, e.g. as disclosed in WO-A-9802445, as well as the DuPHOS [U.S. Pat. No. 5,171,892] and BPE [U.S. Pat. No. 5,008,547] series of bisphospholanes, 14 and 15, respectively. The latter ligands constitute the most preferred class of diphosphines for the asymmetric hydrogenation process described herein.

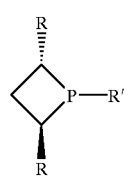

13

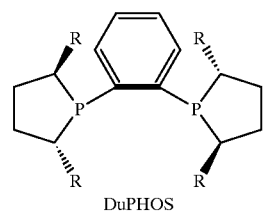

DuPHOS

14

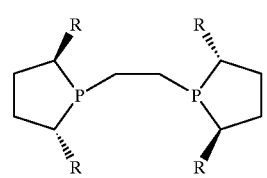

BPE

15

The possession of a series of homologous ligands of types 11–15 which are substituted with a range of different R groups is crucial for success in asymmetric hydrogenations since it is difficult to predict which catalyst will hydrogenate a particular substrate type with high selectivity. For a given substrate, enantioselectivities may be dependent upon the nature of the R-substituent attached to the carbocyclic ring of the DuPHOS, BPE or other ligand (as can be seen from Table 1, below). Typically, a range of ligand-metal complexes may be screened, in order to identify the optimum catalyst for a given transformation, although such screening is readily done by one of ordinary skill in the art, if necessary with reference to the guidance provided herein. The appropriate complex may change, from substrate type to substrate type: rhodium complexes containing certain DuPHOS and BPE ligands have been shown to hydrogenate several types of olefinic substrates, such as enamides, with very high enantioselectivity [Burk et al., *J. Am. Chem. Soc.*, 1993, 115, 10125], while other substrates such as α,β-unsaturated carboxylic acids and allylic alcohols are reduced with only very low selectivities. For example, both β-substituted and β,β-disubstituted α-enamide esters maybe hydrogenated to α-amino acid derivatives with high enantioselectivity using certain DuPHOS and BPE-rhodium catalysts [Burk et al., *J. Am. Chem. Soc.*, 1995, 117, 9375]. Furthermore, β-substituted α-arylenamides may be hydrogenated to α-arylalkylamine derivatives with high enantioselectivities [Burk et al., *J. Am. Chem. Soc.*, 1996, 118, 5142], yet β,β-disubstituted α-arylenamides are hydrogenated with the same catalysts with very low enantioselectivity (0–5% ee).

One embodiment of the present invention is a complete process for the preparation of 2-substituted succinate derivatives (2) from itaconate substrates 7 and 8, which are easily accessed via the Stobbe condensation. This process involves highly enantioselective hydrogenation of itaconate substrates 7 and 8, together as an E/Z mixture or independently, and in the presence or absence of isomerised compound 9. For the hydrogenation, either cationic or neutral rhodium complexes containing the above mentioned chiral phosphine ligands 11–15 may be employed. Apparently, if the ligand is of the bisphospholane type, of formula 14 or 15, it is more likely that, if it can be formed, isomerised product 9 will not be hydrogenated.

Also embodied within the invention is a product isolation and purification protocol, whereby the crude hydrogenation product may be conveniently separated from remaining isomerised compound 9. This protocol entails conversion of the isomerised compound 9 into a more readily separable compound. An example of this method involves treatment of the hydrogenation product mixture, composed of desired product 2 and isomerised compound 9, with a basic iodine solution, leading to iodolactonisation of 9 while leaving 2 unreacted. Basic extractive procedures allow facile separation of the desired product 2 (remains in basic aqueous phase) and remaining impurities (e.g., neutral iodolactonised products of 9) and allows isolation of the 2-substituted succinate in a very pure form. Yield and enantiomeric excess of the product 2 are not affected by this procedure. Further purification of the desired 2-substituted succinate 2 may be accomplished through formation of salts (i.e., amine salt formation through addition of amines to carboxylic acid 2) and subsequent recrystallisation.

The use of a precursor salt is particularly preferred in the case where the hydrogenation substrate is a β,β-disubstituted itaconate derivative, for example wherein $R^3=R^4$=methyl. Otherwise, it may be that high substrate conversion is difficult to achieve at acceptable S/C ratios (typically>200:1). See, for example, Examples 18 and 19. In the former, hydrogenation of the tert-butylamine salt of 2-isopropylidenesuccinic acid 1-methyl ester, catalysed by a rhodium(I) complex of (R,R)-methyl BPE, with S/C=500:1, was conducted at 0° C. using methanol as solvent. This gave complete substrate conversion after 20 hours, to afford after salt cracking (R)-2-isopropylsuccinic acid 1-methyl ester in 95% ee. Enrichment of the salt to at least 99% ee could then be simply achieved by reslurrying in fresh solvent and then filtering. In Example 19, reaction of the free acid of of 2-isopropylidenesuccinic acid 1-methyl ester under similar conditions, with a higher catalyst loading (S/C=300:1), gave only 33% substrate conversion, with (R)-2-isopropylsuccinic acid 1-methyl ester produced in 88% ee.

Overall, the present invention provides a straightforward process for the synthesis of valuable, highly enantiomerically enriched 2-substituted succinates, starting from readily available, inexpensive starting materials.

The following Examples illustrate the invention. Example 17 also illustrated removal of unwanted regioisomer. Preparations 1 to 7 illustrate the preparation of starting materials.

TBME=tert-butyl methyl ether
GC=gas chromatographic analysis

Preparation 1

2-Isobutylidenesuccinic acid mono-methyl ester

Potassium tert-butoxide (988 g, 8.8 mol) was dissolved in 6 L tert-butanol. To this solution was added a mixture of 577 g (8 mol) isobutyraldehyde and 1.46 kg (10 mol) dimethyl succinate in 1 L tert-butanol over a period of 1 h. The mixture was heated to 50° C. for 2 h and stirring was continued at room temperature overnight. The solvent was removed on a rotary evaporator, the residue dissolved in 5 L water and extracted twice with 1 L ethyl acetate. The aqueous phase was acidified with concentrated hydrochloric acid and the organic layer was separated. The aqueous phase was extracted twice with 2 L ethyl acetate. The combined organic phases were dried over magnesium sulfate, filtered and the solvent was removed under reduced pressure, yielding 1.468 kg (98%) of a yellow oil. $^1$H-NMR indicated ~60% of the E-isomer, ~13% Z-isomer, ~19% isomerised material and ~8% of another olefinic compound.

Treatment of this crude material with 2 L pentane induced crystallisation. The crystals were filtered off, washed twice with 300 ml pentane and dried in vacuo. 658 g (44%) of a light yellow, sticky solid was obtained. $^1$H-NMR indicated ~82% of the E-isomer, ~7% Z-isomer, ~11% isomerised material.

Preparation 2

2-Isobutylidenesuccinic acid mono-ethyl ester

To a solution of 11.2 g (0.1 mol) potassium tert-butoxide in 100 ml tert-butanol was added a mixture of 17.4 g (0.1 mol) diethyl succinate and 7.2 g (0.1 mol) isobutyraldehyde over a period of 30 min. The mixture was allowed to stir at room temperature for one hour and heated to 50° C. for an additional hour. The solvent was removed under reduced pressure, the residue was dissolved in 100 ml water and transferred into a separation funnel. The solution was extracted twice with 50 ml ethyl acetate to remove neutral impurities, acidified with 6M HCl and extracted again twice with 20 ml of ethyl acetate. The combined organic phases were dried over magnesium sulfate, filtered and concentrated under reduced pressure, to give 13.6 g (68%) of a yellow brown oil. $^1$H-NMR: 59% E-isomer, 19% Z-isomer, 22% isomerised material.

Preparation 3

2-(Cyclohexylmethylidene)succinic acid mono-ethyl ester

To a solution of 11.2 g (0.1 mol) potassium tert-butoxide in 100 ml tert-butanol was added a mixture of 17.4 g (0.1 mol) diethyl succinate and 11.2 g (0.1 mol) cyclohexylcarboxaldehyde over a period of 30 min. The mixture was allowed to stir at room temperature for one hour and heated to 50° C. for an additional hour. The solvent was removed under reduced pressure, the residue was dissolved in 100 ml water and transferred into a separation funnel. The solution was extracted twice with 50 ml ethyl acetate to remove neutral impurities, acidified with 6M HCl and extracted again twice with 20 ml of ethyl acetate. The combined organic phases were dried over magnesium sulfate, filtered and concentrated under reduced pressure, to give 18.9 g (79%) of a yellow brown oil. $^1$H-NMR: 66% E-isomer, 13% Z-isomer, 15% cyclohexenyl-isomer, 6% other unsaturated olefelinic compound.

Preparation 4

2-(2,2,2-Trimethylethylidene)succinic acid monomethyl ester

To a solution of 11.2 g (0.1 mol) potassium tert-butoxide in 100 ml tert-butanol was added a mixture of 14.6 g (0.1 mol) dimethyl succinate and 8.6 g (0.1 mol) trirnethylacetaldehyde over a period of 30 min. The mixture was allowed to stir at room temperature for one hour and heated to 50° C. for an additional hour. The solvent was removed under reduced pressure, the residue was dissolved in 100 ml water and transferred into a separation funnel. The solution was extracted twice with 50 ml ethyl acetate to remove neutral impurities, acidified with 6M HCl and extracted again twice with 20 ml of ethyl acetate. The combined organic phases were dried over magnesium sulfate, filtered and concentrated under reduced pressure, to give 14.9 g (75%) of a light yellow creamy solid. $^1$H-NMR:>95% E-isomer.

Preparation 5

2-Isopropylidenesuccinic acid mono-ethyl ester

To a solution of 11.2 g (0.1 mol) potassium tert-butoxide in 100 ml tert-butanol was added a mixture of 17.4 g (0.1 mol) diethyl succinate and 5.6 g (0.1 mol) acetone over a period of 5 min. The mixture was allowed to stir at room temperature for 10 minutes. The solvent was removed under reduced pressure, the residue was dissolved in 100 ml water and transferred into a separation funnel. The solution was extracted twice with 50 ml ethyl acetate to remove neutral impurities, acidified with 6M HCl and extracted again twice with 20 ml of ethyl acetate. The combined organic phases were dried over magnesium sulfate, filtered and concentrated under reduced pressure, to give 15.8 g (85%) of a brown oil. $^1$H-NMR: 86% conjugated, 14% deconjugated product.

Preparation 6

2-Cyclohexylidenesuccinic acid mono-ethyl ester

To a solution of of 17.4 g (0.1 mol) diethyl succinate and 9.8 g (0.1 mol) cyclohexanone in 100 ml tert-butanol was added 11.2 g (0.1 mol) potassium tert-butoxide in one portion. The mixture was allowed to stir at room temperature for 30 min. 10 ml of water were added and the solvent was removed under reduced pressure. The residue was dissolved in 100 ml water and transferred into a separation funnel. The solution was extracted twice with 50 ml ethyl acetate to remove neutral impurities, acidified with 6M HCl and extracted again twice with 20 ml of ethyl acetate. The combined organic phases were dried over magnesium sulfate, filtered and concentrated under reduced pressure to give 18.5 g (82%) of a thick yellow oil. $^1$H-NMR: 86% conjugated, 14% deconjugated product.

EXAMPLES 1 TO 16

A solution of 4 mmol of the crude product of one of Preparations 1 to 6, and 3 mmol sodium methanolate in 7 ml degassed methanol, was transferred into a nitrogen-purged 25 ml bomb. The bomb was pressurised three times with 5 atm of hydrogen and subsequently the catalyst (solution in 1 ml of methanol) was injected. The mixture was allowed to stir at room temperature, under a hydrogen pressure of 503 kPa (73 psi) in Examples 1 to 12, 310 kPa (45 psi) in Example 13 and 1034 kPa (150 psi) in Examples 14 to 16. The S:C ratio was 1000:1 in Examples 1 to 12, and 500:1 in Examples 13 to 16.

After the reaction, the pressure was released and the solvent was removed in vacuo. The residue was treated with 10 ml 1M hydrochloric acid and the product was extracted three times with 5 ml dichioromethane. The combined organic phases were dried over magnesium sulfate, filtered and the solvent was removed in vacuo. Enantiomeric excess was determined by GC or HPLC using a chiral stationary phase.

Results are shown in Table 1. Conversion was determined based on E- and Z-isomers. n.d.=not determined. In all cases examined, the R,R catalyst afforded (S)-2-alkylsuccinate, while S,S catalyst furnished the R isomer.

TABLE 1

| Ex. | substrate | catalyst | time [h] | conv. [%] | ee [%] |
|---|---|---|---|---|---|
| 1 | MeO$_2$C-C(=CHCH(CH$_3$)$_2$)-CH$_2$-CO$_2$H | [(Me-BPE)Rh(COD)]OTf | 1 | 100 | 47 |

TABLE 1-continued

| Ex. | substrate | catalyst | time [h] | conv. [%] | ee [%] |
|---|---|---|---|---|---|
| 2 | MeO₂C–C(=CHCH(CH₃)₂)–CH₂–CO₂H | [(Et-BPE)Rh(COD)]BF₄ | 1 | 100 | 80 |
| 3 | MeO₂C–C(=CHCH(CH₃)₂)–CH₂–CO₂H | [(iPr-BPE)Rh(COD)]BF₄ | 2.5 | 28 | 97 |
| 4 | MeO₂C–C(=CHCH(CH₃)₂)–CH₂–CO₂H | [(Me-DuPHOS)Rh(COD)]BF₄ | 1 | 100 | 94 |
| 5 | MeO₂C–C(=CHCH(CH₃)₂)–CH₂–CO₂H | [(Et-DuPHOS)Rh(COD)]BF₄ | 1 | 100 | 99.5 |
| 6 | MeO₂C–C(=CHCH(CH₃)₂)–CH₂–CO₂H | [(PhP(cyclobutane-Et,Et))₂Rh(COD)]BF₄ | 1 | 100 | 79 |
| 7 | MeO₂C–C(=CHCH(CH₃)₂)–CH₂–CO₂H | [(PhP(cyclopentane-Et,Et))₂Rh(COD)]BF₄ | 1 | 100 | 59 |
| 8 | EtO₂C–C(=CHCH(CH₃)₂)–CH₂–CO₂H | [(Me-DuPHOS)Rh(COD)]BF₄ | 1 | 100 | 96 |
| 9 | EtO₂C–C(=CH–cyclohexyl)–CH₂–CO₂H | [(Me-DuPHOS)Rh(COD)]BF₄ | 1 | 100 | 56 |

TABLE 1-continued

| Ex. | substrate | catalyst | time [h] | conv. [%] | ee [%] |
|---|---|---|---|---|---|
| 10 | (cyclohexyl-CH=C(CO₂Et)-CH₂-CO₂H) | [(Et-DuPHOS)Rh(COD)]BF₄ | 1 | 100 | 98 |
| 11 | (tBu-CH=C(CO₂Me)-CH₂-CO₂H) | [(Me-DuPHOS)Rh(COD)]BF₄ | 1 | 100 | 92 |
| 12 | (tBu-CH=C(CO₂Me)-CH₂-CO₂H) | [(Et-DuPHOS)Rh(COD)]BF₄ | 1 | 100 | 99 |
| 13 | (Me₂C=C(CO₂Et)-CH₂-CO₂H) | [(Me-BPE)Rh(COD)]OTf | 5 | 80 | 91 |
| 14 | (Me₂C=C(CO₂Et)-CH₂-CO₂H) | [(Me-BPE)Rh(COD)]OTf | 66 | 100 | 90 |
| 15 | (Me₂C=C(CO₂Et)-CH₂-CO₂H) | [(Me-DuPHOS)Rh(COD)]BF₄ | 66 | 82 | 71 |
| 16 | (cyclohexylidene=C(CO₂Et)-CH₂-CO₂H) | [(Me-BPE)Rh(COD)]OTf | 16 | n.d. | 88 |

EXAMPLE 17

Asymmetric Hydrogenation

To a solution of 532 g (2.86 mol) 2-isobutylenesuccinic acid monomethyl ester (82.7:11 mixture from Preparation 1) in 4.5 L methanol was added 96 g (1.72 mol) sodium methoxide. The mixture was transferred into a 7 L hydrogenation vessel. The mixture was degassed with nitrogen for 2 h and after this pressurised five times with 517 kPa (75 psi) hydrogen under stirring (5 min each). A solution of 540 mg (0.89 mmol) [((R)-MeDuPHOS)Rh(COD)]BF₄ in 20 ml methanol was added and the mixture was allowed to stir under a hydrogen pressure of 200–520 kPa (30–75 psi) for 8 h. NMR analysis revealed that both E- and Z-isomers were hydrogenated and that the 2-isobutenylsuccinic acid monomethyl ester remained unaffected. The enantiomeric excess of the crude 2-isobutylsuccinic acid monomethyl ester was determined to be 94%.

Purification by Iodolactonisation

The reaction mixture was concentrated to a volume of ~1 L; 500 ml water, 101 g (1.2 mol) sodium hydrogen carbonate and 119 g (0.47 mol) iodine were added and the mixture was allowed to stir at room temperature for 16 h. Solid sodium sulfite was added to the mixture in order to destroy the excess iodine. The mixture was concentrated on a rotary evaporator to a volume of ~1 L and extracted three times with 0.5 L ethyl acetate. The aqueous phase was acidified with concentrated hydrochloric acid and again extracted three times with 300 ml ethyl acetate. Analysis of the combined organic layers showed only 2-isobutylsuccinic acid monomethyl ester, 94% ee.

Crystallisation

The solution above was diluted with 1 L ethyl acetate, and a solution of 219 g (3 mol) tert-butylamine in 200 ml ethyl acetate was added over a period of 2 h. The very thick mixture was allowed to stir for an additional 2 h at room temperature. The precipitated solid was filtered, washed three times with 2 L ethyl acetate and dried in vacuo, to give 465 g (71% yield) white powder; >99% ee.

Preparation 7 tert-butylamine salt of 2-isopropylidene succinic acid 1-methyl ester

A solution of tert-butylamine (124 mL, 1.19 mol) in tert-butyl methyl ether (TBME; 100 mL) was added dropwise, at room temperature, over a period of 2 hours, to a solution of 2-isopropylidenesuccinic acid 1-methyl ester (205 g, 1.19 mol) in TBME (350 mL). The resulting thick suspension was stirred at room temperature for an additional hour, then the solid precipitate was collected, washed with TBME (1 L) and dried under vacuum at 40° C. for 48 hours to give 181 g of the salt as a white powder (yield: 62%).

EXAMPLE 18

A solution of the tert-butylamnine salt of 2-isopropylidenesuccinic acid 1-methyl ester (162 g, 0.66 mol) in methanol (800 mL) was transferred to a 2 L high pressure hydrogenation vessel and degassed by pressurizing and venting four times with 10 bar of hydrogen. The vessel was then cooled to 0° C. and a solution of [Rh(COD)(S,S)-Me-BPE]OTf(0.80 g, 0.0013 mol) in methanol (10 mL) was added through the solvent port. The reaction was purged again with hydrogen and stirred at 0° C. under a pressure of hydrogen of 10-7 bar. After 22 hours, the temperature was allowed to raise to room temperature, the vessel was vented in a fume hood, the reaction mixture was transferred to a round-bottomed flask and the solvent was evaporated under reduced pressure. A sample (1 g) of the resulting solid residue was partitioned between HCl 2N (5 mL) and ethyl acetate (5 mL). The organic layer was dried over $MgSO_4$ and evaporated to give 2-(S)-isopropylsuccinic acid 1-methyl ester, ee 96% by GC. The bulk residue was suspended in ethyl acetate (600 mL) and stirred at room temperature for 48 hours, then collected and dried under vacuum to give 154 g of the tert-butylamine salt of 2-(S)-isopropylsuccinic acid monomethyl ester (yield: 94%). A sample (1 g) of the salt was worked up and analyzed as above, indicating an enantiomeric excess of 99% for the free acid.

EXAMPLE 19

2-Isopropylidenesuccinic acid 1-methyl ester (0.86 g, 5.0 mmol) and sodium methoxide (0.10 g, 1.8 mmol) were placed in a 60 mL high pressure hydrogenation vessel and the vessel was purged with hydrogen (by pressurizing and venting three times with 10 bar of hydrogen). Methanol (9 mL, previously degassed by bubbling nitrogen for one hour at room temperature under stirring) was added through the solvent port and the vessel was then cooled to 0° C. A solution of [Rh(COD)(R,R)Me-BPE]OTf (0.010 g, 0.016 mmol, substrate/catalyst: 300/1) in methanol (1 mL) was added and the reactor was charged with 10 bar of hydrogen. The reaction was stirred at 0° C. for 20 hours, then the solvent was evaporated under reduced pressure and the residue was partitioned between HCl 2N (20 mL) and ethyl acetate (20 mL). The organic layer was separated, dried over $MgSO_4$, evaporated to give a pale yellow oil. $^1H$ NMR analysis of the crude indicated that the reduced product and the starting material were present in a ratio 33:67. The enantiomeric excess of 2-(R)-isopropylsuccinic acid 1-methyl ester was 88% by GC. This result shows that, for this particular substrate, the salt form used in Example 18 is preferable.

EXAMPLE 20

The tert-butyl ammonium salt of 2-isopropylidenesuccinic acid 1-methyl ester(0.80 g, 3.3 mmol) was placed in a 60 mL high pressure hydrogenation vessel and the vessel was purged with hydrogen (by pressurizing and venting three times with 10 bar of hydrogen). Methanol (9 mL, previously degassed by bubbling nitrogen for one hour at room temperature under stirring) was added through the solvent port and the vessel was then cooled to 0° C. A solution of [Rh(COD)(R,R)Me-BPE]OTf (0.004 g, 0.0065 mmol, substrate/catalyst: 500/1) in methanol (1 mL) was added and the reactor was charged with 10 bar of hydrogen. The reaction was stirred at 0° C. for 20 hours, then the solvent was evaporated under reduced pressure and the residue was partitioned between HCl 2N (20 mL) and ethyl acetate (20 mL). The organic layer was separated, dried over $MgSO_4$, evaporated to give a pale yellow oil. $^1H$ NMR analysis of the crude indicated that the conversion to the reduction product was more than 95%. The enantiomeric excess of 2-(R)-isopropylsuccinic acid 1-methyl ester was 95% by GC.

EXAMPLE 23

The tert-butylamine salt of (E)-2-(3-phenyl-2-propenylidene)succinic acid 1-methyl ester (1 g, 4.1 mmol) and [Rh(COD)(R,R)Me-DuPhos]$BF_4$ (6 mg, 0.01 mmol, substrate/catalyst: 400: 1) were weighed in a 60 mL high pressure hydrogenation vessel and an atmosphere of nitrogen was introduced by evacuating the reactor and refilling with oxygen-free dry nitrogen. This procedure was repeated three times. Methanol (5 mL, previously degassed by bubbling nitrogen for one hour at room temperature while stirring) was added to the reactor through the solvent port. The reactor was charged with 690 kPa (100 psi) of hydrogen and the pressure released. The reactor was then repressurised to 965 kPa (140 psi) and the reaction was stirred for 16 hours, then the solvent was evaporate under reduced pressure and the residue was partitioned between HCl 2N (20 mL) and ethyl acetate (20 mL). The organic layer was separated, dried over $MgSO_4$, evaporated to give a pale yellow oil. $^1H$ NMR analysis of the crude indicated that the conversion to the reduction product was complete. The enantiomeric excess of 2-(S)-(3-phenyl-2-propenyl)succinic acid 1-methyl ester was 99% by GC.

EXAMPLE 22

The tert-butylamine salt of 2-cyclohexylidenesuccinic acid 1-methyl ester (0.91 g, 3.2 mmol) was placed in a 60 mL high pressure hydrogenation vessel and the vessel was purged with hydrogen (by pressurizing and venting three times with 10 bar of hydrogen). Methanol (9 mL, previously degassed by bubbling nitrogen for one hour at room temperature under stirring) was added through the solvent port and the vessel was then cooled to 0° C. A solution of [Rh(COD)(RR)Me-BPE]OTf (0.004 g, 0.0065 mmol, substrate/catalyst: 500/1) in methanol (1 mL) was added and the reactor was charged with 10 bar of hydrogen. The reaction was stirred at 0° C. for 20 hours, then the solvent was evaporated under reduced pressure and the residue was partitioned between HCl 2N (20 mL) and ethyl acetate (20 mL). The organic layer was separated, dried over $MgSO_4$, evaporated to give 0.75 g of 2-cyclohexylsuccinic acid monomethyl ester as a pale yellow oil (yield 82%). The enantiomeric excess of 2-(R)-cyclohexylsuccinic acid 1-methyl ester was 96% by GC.

EXAMPLE 23

The tert-butylamine salt of2-(2-adamantylidene)succinicacid 1-methyl ester(0.54 g, 1.6 mmol) was placed in a 60 mL high pressure hydrogenation vessel and the vessel was purged with hydrogen (by pressurizing and venting three times with 10 bar of hydrogen). Methanol (9 mL, previously degassed by bubbling nitrogen for one hour at room temperature under stirring) was added through the solvent port and the vessel was then cooled to 0° C. A solution of [Rh(COD)(R,R)Me-BPE]OTf (0.004 g, 0.0065 mmol, substrate/catalyst: ~250/1) in methanol (1 mL) was added and the reactor was charged with 10 bar of hydrogen. The reaction was stirred at 0° C. for 23 hours, then the solvent was evaporated under reduced pressure and the residue was partitioned between HCl 2N (20 mL) and ethyl acetate (20 mL). The organic layer was separated, dried over $MgSO_4$, evaporated to give a pale yellow oil. $^1H$ NMR analysis of the crude indicated that the conversion to the reduction product was complete. The enantiomeric excess of 2-(R)-2-adamantanyl)succinic acid monomethyl ester was 78% by GC. In similar experiments, carried out at room temperature (approx. 20° C.), 2-(R)-(2-adamantanyl) succinic acid monomethyl ester was obtained with 63% ee.

What is claimed is:

1. A process for the preparation of an enantiomerically enriched 2-substituted succinic acid deriviative of formula 2, which comprises asymmetric hydrogenation of the dehydro precursor of formula 7 or 8, or a mixture thereof

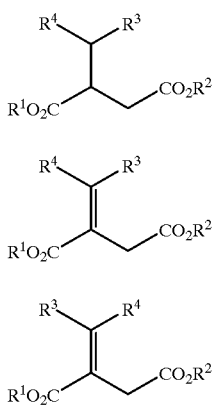

wherein $R^1$ and $R^2$ are independently selected from the group consisting of H, a salt-forming cation, and an organic group of up to 30 C atoms, and $R^3$ and $R^4$ are independently selected from H or an organic group of up to 30 C atoms, provided that $R^3$ and $R^4$ are not both H, wherein said asymmetric hydrogenation is carried out in the presence of a transition metal complex of a chiral phosphine ligand having the formula 10

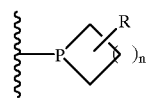

wherein n is 0 to 6 and R represents at least one non-hydrogen organic group of up to 30 C atoms; wherein said transition metal is selected from the group consisting of rhodium, ruthenium, and iridium.

2. The process, according to claim 1, wherein said precursor is a salt.

3. The process, according to claim 2, wherein said precursor is an amine or phosphine salt.

4. The process, according to claim 3, wherein said precursor is an amine salt.

5. The process, according to claim 4, wherein said amine is a primary amine.

6. The process, according to claim 5, wherein said amine is tert-butylamine.

7. The process, according to claim 4, wherein said amine is a tertiary amine.

8. The process, according to claim 7, wherein said amine is triethylamine.

9. The process, according to claim 3, wherein said precursor salt is isolated prior to use in said process.

10. The process, according to claim 2, wherein a metal salt of said precursor is generated in situ.

11. The process, according to claim 1, wherein said ligand is of formula 11 or 12

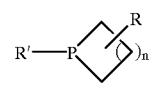

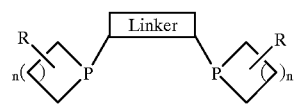

wherein Linker and R' are independently any non-hydrogen organic group of up to 30 C atoms.

12. The process, according to claim 11, wherein the ligand is of formula 14 or 15

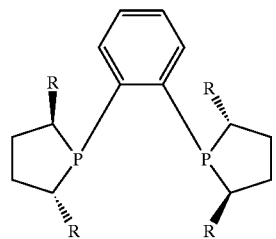

DuPHOS

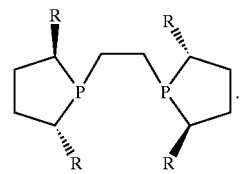

BPE

13. The process, according to claim 12, wherein R is a $C_{1-8}$ linear or branched alkyl group, or an aromatic group.

14. The process, according to claim 1, wherein $R^3$ and $R^4$ are each, or are linked to form, an organic group of up to 30 C atoms.

15. The process, according to claim 14, wherein $R^3=R^4$.

16. The process, according to claim 1, wherein one of $R^3$ and $R^4$ is H.

17. The process, according to claim 1, wherein $R^3$ and $R^4$ are independently selected from the group consisting of H, $C_{1-20}$ alkyl, and aralkyl.

18. The process, according to claim 1, wherein $R^2$ is H or a cation.

19. The process, according to claim 18, wherein $R^1$ is $C_{1-10}$ alkyl or aralkyl.

20. The process, according to claim 1, wherein said transition metal is rhodium.

21. The process, according to claim 1, wherein the reaction temperature is less than 10° C.

22. The process, according to claim 1, wherein the product 2 has an enantiomeric excess of at least 90%.

23. A process for the preparation of an enantiomerically enriched 2-substituted succinic acid derivative of formula 2, which comprises asymmetric hydrogenation of the dehydro precursor of formula 7 or 8, or a mixture thereof $$R^1O_2C\text{-}C(R^4)(R^3)\text{-}CH\text{-}CO_2R^2 \quad \mathbf{2}$$

$$R^1O_2C\text{-}C(=CR^3R^4)\text{-}CH_2\text{-}CO_2R^2 \quad \mathbf{7}$$

$$R^1O_2C\text{-}C(=CR^4R^3)\text{-}CH_2\text{-}CO_2R^2 \quad \mathbf{8}$$

wherein $R^1$ and $R^2$ are independently selected from the group consisting of H, a salt-forming cation, and an organic group of up to 30 C atoms, and $R^3$ is selected from H or an organic group of up to 30 C atoms, and wherein $R^4$ is $CHR^5R^6$, $R^5$ and $R^6$ each being H or any other group consistent with the definition of $R^4$, wherein said asymmetric hydrogenation takes place in the presence of a transition metal complex of a chiral phosphine ligand having the formula $$\text{10}$$

wherein n is 0 to 6 and R represents at least one non-hydrogen organic group of up to 30 C atoms; wherein said transition metal is selected from the group consisting of rhodium, ruthenium, and iridium; conversion of the isomerised compound 9

$$R^1O_2C\text{-}CH(R^3)\text{-}C(R^5)=C(R^6)\text{-}CO_2R^2 \quad \mathbf{9}$$

into a compound readily separable from the hydrogenation product 2; and removal of said separable compound.

24. The process, according to claim 23, wherein the conversion comprises treatment of the isomerised substrate 9 with basic iodine, to give a lactone derivative, and the removal comprises extraction.

25. The process, according to claim 23, wherein said precursor is a salt.

26. The process, according to claim 25, wherein said precursor is an amine or phosphine salt.

27. The process, according to claim 26, wherein said precursor is an amine salt.

28. The process, according to claim 26, wherein said amine is a primary amine.

29. The process, according to claim 28, wherein said amine is tert-butylamine.

30. The process, according to claim 26, wherein said amine is a tertiary amine.

31. The process, according to claim 30, wherein said amine is triethylamine.

32. The process, according to claim 23, wherein said precursor salt is isolated prior to use in said process.

33. The process, according to claim 23, wherein a metal salt of said precursor is generated in situ.

34. The process, according to claim 23, wherein the ligand is as defined in claim 1.

35. The process, according to claim 23, wherein said ligand is of formula 11 or 12

$$\text{11}$$

$$\text{12}$$

wherein Linker and R' are independently any non-hydrogen organic group of up to 30 C atoms.

36. The process, according to claim 23, wherein the ligand is of formula 14 or 15

$$\text{14 (DuPHOS)}$$

$$\text{15 (BPE)}$$

37. The process, according to claim 36, wherein R is a $C_{1-8}$ linear or branched alkyl group, or an aromatic group.

38. The process, according to claim 23, wherein $R^3$ and $R^4$ are each, or are linked to form, an organic group of up to 30 C atoms.

39. The process, according to claim 38, wherein $R^3=R^4$.

40. The process, according to claim 23, wherein one of $R^3$ and $R^4$ is H.

41. The process, according to claim 23, wherein $R^3$ and $R^4$ are independently selected from the group consisting of H, $C_{1-20}$ alkyl, and aralkyl.

42. The process, according to claim 23, wherein $R^2$ is H or a cation.

43. The process, according to claim 42, wherein $R^1$ is $C_{1-10}$ alkyl or aralkyl.

44. The process, according to claim 23, wherein said transition metal is rhodium.

45. The process, according to claim 23, wherein the reaction temperature is less than 10° C.

46. The process, according to claim 23, wherein the product 2 has an enantiomeric excess of at least 90%.

47. The process, according to claim 1, wherein the starting material is obtained by Stobbe condensation which is then treated without separation of geometric isomers.

48. The process, according to claim 23, wherein the starting material is obtained by Stobbe condensation which is then treated without separation of geometric isomers.

\* \* \* \* \*